(12) United States Patent
Bedau

(10) Patent No.: US 12,131,057 B2
(45) Date of Patent: Oct. 29, 2024

(54) ENCODING AND INTEGRITY MARKERS FOR MOLECULAR STORAGE APPLICATIONS

(71) Applicant: Western Digital Technologies, Inc., San Jose, CA (US)

(72) Inventor: Daniel Bedau, San Jose, CA (US)

(73) Assignee: Western Digital Technologies, Inc., San Jose, CA (US)

( * ) Notice: Subject to any disclaimer, the term of this patent is extended or adjusted under 35 U.S.C. 154(b) by 187 days.

(21) Appl. No.: 17/649,291

(22) Filed: Jan. 28, 2022

(65) Prior Publication Data

US 2023/0244412 A1 Aug. 3, 2023

(51) Int. Cl.
*G06N 3/00* (2023.01)
*G06F 3/06* (2006.01)

(52) U.S. Cl.
CPC .......... *G06F 3/0655* (2013.01); *G06F 3/0604* (2013.01); *G06F 3/0673* (2013.01)

(58) Field of Classification Search
CPC ..... G06F 3/0655; G06F 3/0604; G06F 3/0673
See application file for complete search history.

(56) References Cited

U.S. PATENT DOCUMENTS

| | | | |
|---|---|---|---|
| 10,902,939 B2 | 1/2021 | Merriman et al. | |
| 2019/0080760 A1 | 3/2019 | Predki et al. | |
| 2020/0185057 A1 | 6/2020 | Leake et al. | |
| 2021/0098081 A1* | 4/2021 | Yekhanin | G06F 16/2365 |
| 2021/0134396 A1* | 5/2021 | Yekhanin | G16B 40/10 |
| 2022/0282283 A1* | 9/2022 | Scott | C12N 15/113 |
| 2022/0364991 A1* | 11/2022 | Wanunu | C12Q 1/6869 |

FOREIGN PATENT DOCUMENTS

| | | |
|---|---|---|
| CN | 109830263 A | 5/2019 |
| CN | 112002376 A | 11/2020 |
| CN | 112288090 A | 1/2021 |
| CN | 110569974 B | 8/2021 |
| CN | 113300720 A | 8/2021 |

(Continued)

OTHER PUBLICATIONS

Dinu das, "DNA Storage is the most important innovation you've never heard about," Jun. 26, 2021 (available at https://bestgamingpro.com/dna-storage-is-the-most-important-innovation-youve-never-heard-about/).

(Continued)

*Primary Examiner* — Min Huang

(57) ABSTRACT

Disclosed herein are molecular storage systems and methods of reading molecules that include integrity markers. A molecular storage system may comprise read hardware configured to read molecules storing data, and at least one processor coupled to the read hardware. The processor is configured to determine whether a molecule being read by the read hardware includes an expected integrity marker, and, in response to a determination that the molecule being read by the read hardware does not include the expected integrity marker, instruct the read hardware to abandon a read operation associated with the molecule being read by the read hardware. The partial readback can be placed in a buffer and used in an assembly process only if an intact molecule is not available.

21 Claims, 3 Drawing Sheets

(56) References Cited

FOREIGN PATENT DOCUMENTS

KR     1020200025430 A    3/2020
WO        2021105974 A1   6/2021

OTHER PUBLICATIONS

Frölich, M., Hofheinz, D. & Meier, M.A.R. "Reading mixtures of uniform sequence-defined macromolecules to increase data storage capacity." Commun Chem 3, 184 (2020).
Hyungtaek Jung et al., "Twelve quick steps for genome assembly and annotation in the classroom," PLOS Computational Biology, https://doi.org/10.1371/journal.pcbi.1008325, Nov. 12, 2020.
Karishma Matange et al., "DNA stability: a central design consideration for DNA data storage systems," Nature Communications, (Mar. 1, 2021) 12:135,| https://doi.org/10.1038/s41467-021-21587-5.
Sara El-Metwally et al., "Next-Generation Sequence Assembly: Four Stages of Data Processing and Computational Challenges," PLOS Computational Biology, | www.ploscompbiol.org, Dec. 2013, vol. 9, Issue 12, e1003345.
International Search Report and Written Opinion from PCT application No. PCT/US2022/030064 (filed May 19, 2022), mailed Oct. 24, 2022.
Lopez, R. et al., "DNA assembly for nanopore data storage readout," Nature Communications, 2019, vol. 10, pp. 1-9.

\* cited by examiner

ENCODING AND INTEGRITY MARKERS FOR MOLECULAR STORAGE APPLICATIONS

BACKGROUND

Nucleic acids are negatively-charged polyelectrolytes with four monomers that are covalently bonded to form polymer chains. For deoxyribonucleic acid (DNA), the monomers are the nucleotides adenine (A), thymine (T), guanine (G), and cytosine (C). For ribonucleic acid (RNA), they are A, C, G, and uracil (U).

The use of biomolecules, including DNA, RNA, and proteins, to store data has been proposed due to the density, stability, energy-efficiency, and longevity of biomolecules. For example, a human cell has a mass of about 3 picograms and stores around 6.4 GB of information. The volumetric density of DNA is estimated to be 1,000 times greater than that of flash memory, and its energy consumption $10^8$ times less than that of flash memory. In addition, the retention time of DNA can be significantly greater than that of electronic memory. Thus, DNA can store information reliably over time.

DNA storage systems may encapsulate and seal DNA within a matrix (e.g., silica), or they may store the encoded DNA in an aqueous solution (e.g., refrigerated or frozen) or as a dry solid. Encapsulation is typically used for data that is accessed infrequently (e.g., once per decade), whereas the use of aqueous solutions is favored for shorter-term storage (e.g., working storage or dynamic storage), where data may be accessed relatively frequently.

There are a number of challenges in molecular storage, including the amount of degradation that occurs when the data is stored and accessed. For example, the freeze-thaw processes for solubilized DNA can lead to breakage due to the formation of ice crystals that can cause mechanical stress, which can be particularly problematic for longer DNA molecules. The handling of liquids containing the molecules (e.g., turbulence caused by moving solutions through pipette tips, microfluidic channels, tubing, etc.) can also lead to breakage. This phenomenon is sometimes referred to as fragmentation.

It can be difficult, expensive, or impossible to know whether a particular molecule that has been read was a complete molecule or a fragment of a larger molecule.

There is, therefore, a need for improvements.

SUMMARY

This summary represents non-limiting embodiments of the disclosure.

In some aspects, the techniques described herein relate to a molecular storage system, including: read hardware configured to read molecules storing data; and at least one processor coupled to the read hardware and configured to: determine whether a molecule being read by the read hardware includes an expected integrity marker; and in response to a determination that the molecule being read by the read hardware does not include the expected integrity marker, instruct the read hardware to abandon a read operation associated with the molecule being read by the read hardware.

In some aspects, the techniques described herein relate to a molecular storage system, wherein the expected integrity marker indicates a beginning of the molecule being read by the read hardware or an end of the molecule being read by the read hardware.

In some aspects, the techniques described herein relate to a molecular storage system, wherein the expected integrity marker includes a unique sequence excluded by a coding scheme used to record data on molecules used in the molecular storage system.

In some aspects, the techniques described herein relate to a molecular storage system, wherein the expected integrity marker includes a sequence that does not naturally occur in molecules of a type used in the molecular storage system.

In some aspects, the techniques described herein relate to a molecular storage system, wherein the expected integrity marker is an intra-molecule integrity marker.

In some aspects, the techniques described herein relate to a molecular storage system, wherein the read hardware includes: a nanopore; at least one electrode for sensing ionic current through the nanopore; and a voltage source coupled to the at least one electrode.

In some aspects, the techniques described herein relate to a molecular storage system, wherein the molecular storage system further includes at least one buffer coupled to the at least one processor, and wherein the at least one processor is further configured to: in response to the determination that the molecule being read by the read hardware does not include the expected integrity marker, store a partial readback result associated with the molecule being read by the read hardware in the at least one buffer.

In some aspects, the techniques described herein relate to a molecular storage system, wherein the partial readback result is one of a plurality of partial readback results, and wherein the at least one processor is further configured to: perform an assembly process using the plurality of partial readback results.

In some aspects, the techniques described herein relate to a molecular storage system, wherein the at least one processor is further configured to: before performing the assembly process, determine that no complete readback of another molecule storing identical data is available.

In some aspects, the techniques described herein relate to a molecular storage system, wherein the expected integrity marker is a first integrity marker, and wherein the at least one processor is further configured to: determine whether the molecule being read by the read hardware includes at least one additional integrity marker; and in response to determining that the molecule being read by the read hardware includes both the first integrity marker and the at least one additional integrity marker, discard the partial readback result associated with the molecule being read by the read hardware.

In some aspects, the techniques described herein relate to a molecular storage system, wherein the expected integrity marker is a first integrity marker, and wherein the at least one processor is further configured to: determine whether the molecule being read by the read hardware includes at least one additional integrity marker; and in response to determining that the molecule being read by the read hardware includes both the first integrity marker and the at least one additional integrity marker, provide a readback result to a calling system.

In some aspects, the techniques described herein relate to a method of reading molecules in a molecular storage system, the method including: determining whether a molecule includes a first integrity marker indicating that a first end of the molecule is intact; in response to determining that the molecule does not include the first integrity marker indicating that the first end of the molecule is intact, abandoning reading of the molecule; in response to determining that the molecule includes the first integrity marker indicating that the first end of the molecule is intact, determining whether the molecule includes a second integrity marker indicating that a second end of the molecule is intact; and in response to determining that the molecule includes the second integrity marker indicating that the second end of the molecule is intact, providing a read result to a requestor.

In some aspects, the techniques described herein relate to a method, further including: in response to determining that the molecule does not include the second integrity marker indicating that the second end of the molecule is intact, storing a partial readback result associated with the molecule.

In some aspects, the techniques described herein relate to a method, wherein the partial readback result is one of a plurality of partial readback results, and wherein the method further includes: performing an assembly process using the plurality of partial readback results.

In some aspects, the techniques described herein relate to a method, further including: before performing the assembly process, determining that no complete readback of another molecule storing identical data is available.

In some aspects, the techniques described herein relate to a method, wherein: the first integrity marker is a forward-ordered integrity marker indicating a beginning of the molecule and the second integrity marker is a forward-ordered integrity marker indicating an end of the molecule, or the first integrity marker is a reverse-ordered integrity marker indicating the end of the molecule and the second integrity marker is a reverse-ordered integrity marker indicating the beginning of the molecule.

In some aspects, the techniques described herein relate to a method, wherein the first integrity marker and the second integrity marker are identical.

In some aspects, the techniques described herein relate to a method, wherein the first integrity marker and the second integrity marker include a unique sequence excluded by a coding scheme used to record data on the molecules in the molecular storage system.

In some aspects, the techniques described herein relate to a method, wherein the first integrity marker and the second integrity marker include a sequence that does not naturally occur in molecules of a type used in the molecular storage system.

In some aspects, the techniques described herein relate to a method, wherein the first integrity marker and the second integrity marker are different.

In some aspects, the techniques described herein relate to a method, further including: determining whether the molecule includes an intra-molecule integrity marker; and in response to determining that the molecule does not include the intra-molecule integrity marker, abandoning reading of the molecule.

BRIEF DESCRIPTION OF THE DRAWINGS

Objects, features, and advantages of the disclosure will be readily apparent from the following description of certain embodiments taken in conjunction with the accompanying drawings in which.

Figure 1:
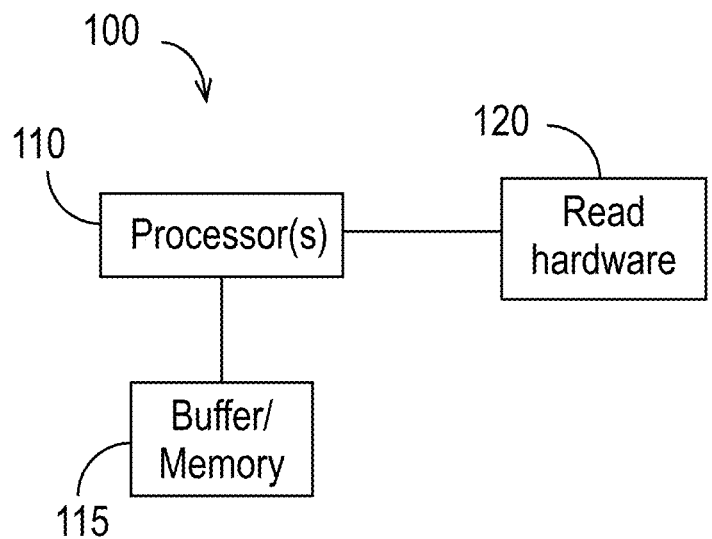
FIG. 1 is a diagram of components of a molecular storage system in accordance with some embodiments.

To facilitate understanding, identical reference numerals have been used, where possible, to designate identical elements that are common to the figures. It is contemplated that elements disclosed in one embodiment may be beneficially utilized in other embodiments without specific recitation. Moreover, the description of an element in the context of one drawing is applicable to other drawings illustrating that element.

DETAILED DESCRIPTION

There are many data storage applications, ranging from archival storage of data intended to be stored and potentially never accessed again (e.g., except in an emergency) to data that is frequently written and read (e.g., on a personal computer). Molecular storage has been considered for many, if not all, of these storage applications.

Classical recording channels store and retrieve information in a fixed order. For example, the message "Hello World" that is familiar from computer-programming courses can be converted to binary format (ignoring the line code, error-correcting codes, etc.) and written and stored as: "01001000 01100101 01101100 01101100 01101111 00100000 01010111 01101111 01110010 01101100 01100100," where each consecutive group of eight bits represents one of the characters of the message. (It is to be appreciated that the spaces in the sequence above are included solely to improve readability of the sequence of bits; the spaces are not intended to suggest there would be any breaks between bits of the message.)

When the message is read back, there may be read errors or erasures. For example, the resulting readback might be: "010010$\epsilon$0 01100101 01101100 01101100 00101111 00100000 01010111 01101110 0111001$\epsilon$01101100 01100100," where "$\epsilon$" represents a bit error or bit erasure. There are many techniques that can be used to identify the errors in readback data (e.g., cyclic redundancy check (CRC) codes, parity checks, etc.), and there are also coding schemes that can correct at least some errors (e.g., forward error correcting (FEC) codes (e.g., Reed-Solomon codes, etc.)).

As explained above, molecular storage systems (e.g., DNA storage systems) suffer from other kinds of failures, including those due to molecular degradation. Depending on the type of system in use, the degradation can be caused by, for example, oxidation, humidity, temperature, radiation, alkylation, and/or hydrolysis (for systems using molecules in an encapsulated physical state); freeze-thaw cycles, reconstitution, rehydration, lyophilization, base mismatches or mutations, oxidation, alkylation, and/or hydrolysis (for systems using frozen, dried, or lyophilized molecules); and/or mechanical shear, buffer salt concentration, buffer pH, temperature, ionizing radiation, and/or base mismatches or mutations (for systems using solubilized molecules). As a result, fragmentation, which occurs when molecules break into pieces, is a problem in molecular storage systems because the order of the pieces is lost.

As an example, the "Hello World" message above could be stored as a DNA or RNA molecule. Because there are four bases in DNA and in RNA, each base can represent two bits (e.g., for DNA, A can represent 00, C can represent 01, G can represent 10, and T can represent 11). Thus, with each consecutive pair of bits represented by a base or, alternatively, an entire oligo, the message can be represented as:

"10201211123012301233020011312331302123012 10," where each of the digits stands for a base or, alternatively, for an entire oligo. Assume a fragmentation error occurs after the message has been stored, and the molecule that stores the message is split into two parts, "23012301233020011312331302123012 10," and "102012111." During the readback, the fragments could be read in an arbitrary order, and it may not be clear what their order should be.

In principle it is possible to recover the original sequence using a process referred to in genetics as "assembly," "sequence alignment," or "stitching." The assembly process relies on a comparison of the individual fragments with a reference genome, or, alternatively, a pair-wise comparison between all of the fragments found, which is computationally expensive. The process can use $O(n^2)$ comparisons and $O(n^2)$ storage locations, where n is the number of reads. Although the amount of computation required to perform assembly may make sense in some applications (e.g., for extremely valuable data or archival storage), it is impractical (e.g., too energy-inefficient) to use assembly for many applications (e.g., working storage or short-term dynamic storage). For example, assembling the human genome might use many MWh of energy to retrieve only a few Gbp (giga-base-pairs). The amount of energy used for the assembly process will be millions of times the amount of energy used to read back data from other storage systems (e.g., a flash drive).

Accordingly, there is a need to develop new techniques to allow more efficient, simpler, and accurate readback in molecular storage systems.

Disclosed herein are systems and methods for adding integrity markers to stored molecules to allow the readback circuitry to determine whether the molecules being read are complete. A plurality of physically redundant molecules are provided, each storing the same information (e.g., an identical set of one or more bits is stored on multiple molecules, the result of which is intended to be that there are multiple identical molecules). During the readback process, if the expected integrity markers are absent from a molecule, or they are present but corrupted, the read procedure being performed on that molecule can be abandoned and the result of the readback placed in a temporary buffer in favor of reading another molecule that is supposed to be storing the identical information. The readback of that molecule can also be buffered temporarily if its integrity markers are missing or corrupted. The readback process continues until (a) a complete molecule is found that includes the expected integrity markers, which indicates that the stored, intact information has been retrieved, or (b) no molecule is found that includes the expected integrity markers. In the case that a molecule is found that includes the expected integrity markers, the partial readback results in the temporary buffer can be discarded, because an intact, complete molecule has been found and read. If, after reading some number of or all of the available molecules, no molecule having all expected integrity markers has been found, the partial readback results in the temporary buffer can be subjected to an assembly process to attempt to recover the information. Thus, the complexity and cost of assembly are undertaken only when the readback circuitry does not encounter a complete molecule that has all expected integrity markers. (Alternatively, of course, the readback can be abandoned altogether if the assembly process is cost/energy-prohibitive given the value of the information that has been corrupted.)

In some embodiments, integrity markers are added to the beginning and end of each stored molecule. The integrity markers may be selected so that they are unique, easily-recognized sequences. For example, the markers may be selected such that their likelihood of occurrence inside of a molecule is sufficiently small, or is specifically excluded by the coding scheme (e.g., one or more particular sequences may be reserved as integrity markers). As another example, an "out of band" marker might be used (e.g., a molecule "4," which does not normally occur (or does not naturally occur) in the sequence). On readback, detection of the integrity markers at the beginning and end of a molecule indicates that the molecule read is intact and complete.

The integrity marker used at the beginning of the molecule may be the same as (identical to) or different from the integrity marker used at the end of the molecule. For example, using the "Hello World" message example, an integrity marker having the form "01230123" may be used at the beginning and the end of the stored message: "01230123 10201211123012301233020011312331302123012 10 01230123." (Once again, the sequence formatting in this document includes spaces for the reader's convenience.) Detection of the sequence "01230123" at the beginning of the read operation indicates that the beginning of the molecule is still intact. Detection of the sequence "01230123" at the end of the read indicates that the completed molecule was read. Detection of the sequence "32103210" at the beginning of a read operation indicates that the molecule is being read backwards, and that the end of the molecule is intact; detection of the sequence "32103210" at the end of the read operation indicates that the beginning of the molecule was also intact, and that the complete molecule was read (albeit backwards).

The absence of an integrity marker at the beginning or end of a molecule being read indicates fragmentation of the molecule. As a result, the read operation can be immediately abandoned and the faulty readback data discarded without incurring additional storage or data processing cost. Alternatively, the readback data from molecule fragments might be held back in temporary storage and only used (e.g., subjected to assembly) if no complete segments are found and read.

FIG. 1 is a diagram of components of a molecular storage system 100 in accordance with some embodiments. The molecular storage system 100 comprises at least one processor 110 communicatively coupled to read hardware 120 and to a buffer 115 (e.g., memory). In cooperation with the read hardware 120, the at least one processor 110 reads molecules of the molecular storage system 100 to retrieve data.

Figure 2:
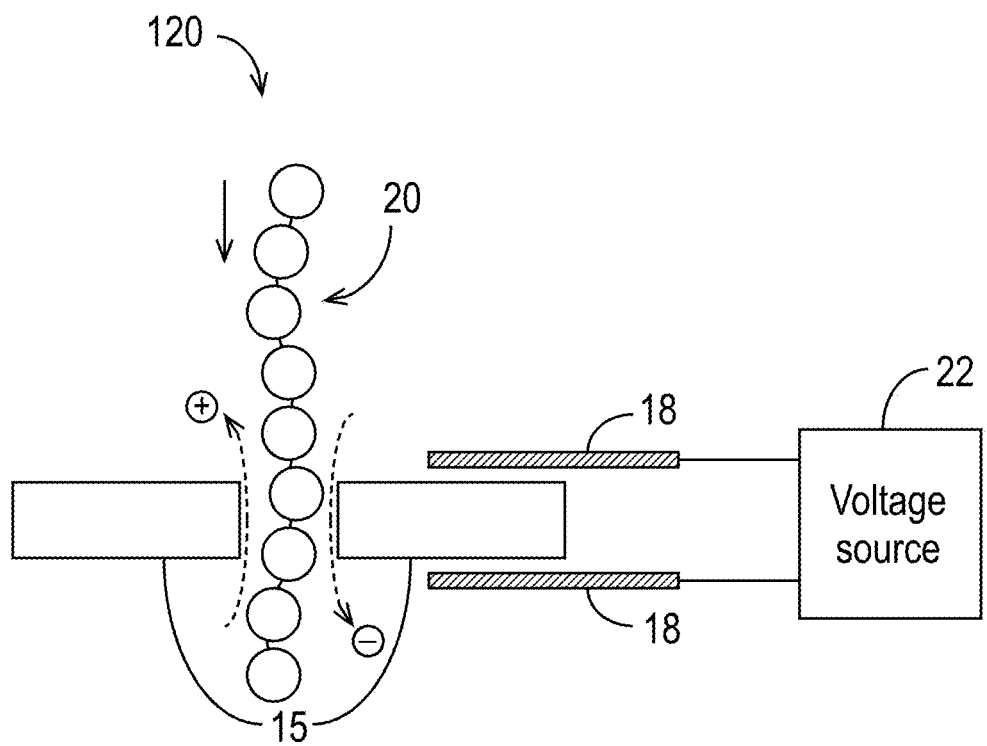
FIG. 2 illustrates an example of read hardware in accordance with some embodiments.

FIG. 2 illustrates an example of the read hardware 120. The example read hardware 120 includes a nanopore 15, two sensing electrodes 18, and a voltage source 22 coupled to the sensing electrodes 18. The nanopore 15 may be a biological nanopore or a solid-state nanopore. A molecule 20, such as a nucleic acid strand to be read, in an electrolyte solution can be driven through the nanopore 15, primarily by electrophoresis, and read. FIG. 2 illustrates a nanopore 15 with a molecule 20 (e.g., a single-stranded DNA (ssDNA) molecule), passing through it. A highly-focused external electric field applied transverse to and in the vicinity of the nanopore 15 (e.g., by the sensing electrodes 18) acts on a relatively short segment of the negatively charged molecule 20 and directs it through the hole in the nanopore 15. The two sensing electrodes 18 are situated near the nanopore 15 to sense the ionic current through the nanopore 15. The sensing electrodes 18 are connected to the voltage source 22, which applies a voltage to the sensing electrodes 18.

As the molecule 20 passes through the nanopore 15, the ions occupying the nanopore 15 are excluded, which causes changes in the ionic current and/or electronic signal measured across the nanopore 15 (e.g., using the sensing electrodes 18 on opposite sides of the nanopore 15), which can be observed and used to detect constituent parts of the molecule 20 (e.g., nucleotides of a DNA strand). For example, as nucleic acid moves through the nanopore 15, different nucleotides cause different ionic current patterns. Specifically, the nucleotides cause distinct, measurable ionic current blockades, or current drops, as they pass through the nanopore 15. The current blockades can be detected and recorded (e.g., using a current amplifier) and converted into digital signals (e.g., using an analog-to-digital converter). These current blockades, or patterns of them, can be used to distinguish between different nucleotides. By analyzing the amplitudes, durations, frequencies, and shapes of the blockade events, the at least one processor 110 can read the molecule 20.

Figure 3:
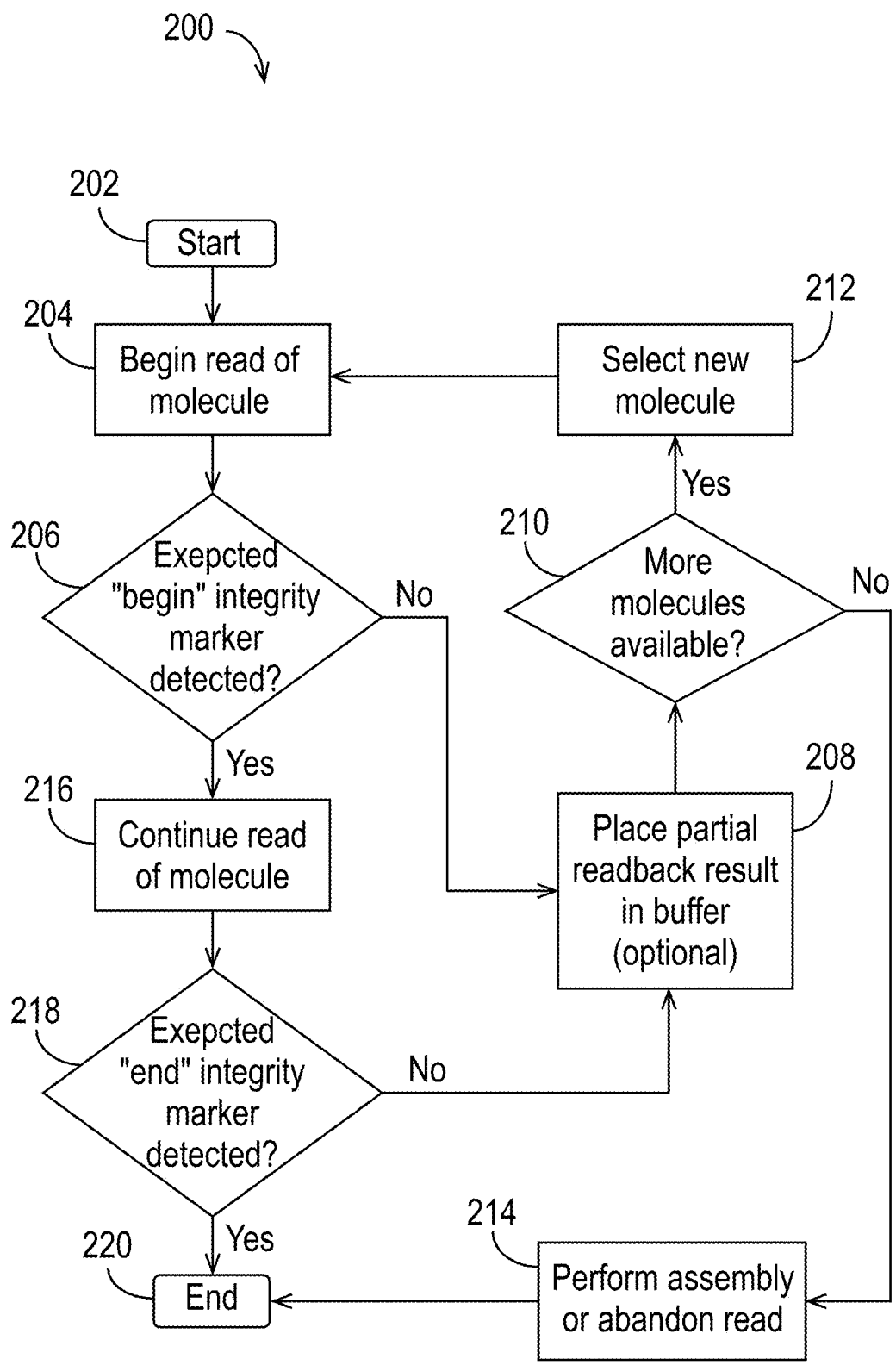
FIG. 3 is a flow diagram illustrating an example of a method performed by a molecular storage system in accordance with some embodiments.

FIG. 3 is a flow diagram illustrating an example of a method 200 performed by a molecular storage system (e.g., the molecular storage system 100) in accordance with some embodiments. At block 202, the method 200 begins. At block 204, the reading of a molecule (e.g., the molecule 20 of FIG. 2) begins. At block 206, it is determined (e.g., by the at least one processor 110 of the molecular storage system 100) whether the expected integrity marker indicating the beginning of a molecule is present. As explained above, the expected integrity marker indicating the beginning of a molecule may be a forward-oriented "begin" integrity marker or a reverse-oriented "end" integrity marker. If the expected integrity marker is not present, at block 208, the in-progress read operation can be abandoned (e.g., by the at least one processor 110 instructing the read hardware 120 to stop the readback process). Optionally, at block 208, the partial readback result may be placed into a buffer. Alternatively, as explained above, the partial readback result may be discarded. At block 210, if more molecules are available to read, the method 200 transitions to block 212, where another molecule is selected (e.g., if using read hardware 120 such as shown in FIG. 2, the voltage source 22 can be activated to draw another molecule 20 into the nanopore 15), and the method 200 returns to block 204. If, at block 210, no more molecules are available, then the method 200 transitions to block 214, where an assembly procedure may be performed to attempt to recover the data (e.g., if the complexity/energy associated with doing so are warranted), or the read attempt may be abandoned altogether.

If, at block 206, the expected integrity marker is detected (e.g., the at least one processor 110 finds either the forward-oriented "begin" integrity marker or a reverse-oriented "end" integrity marker), the method 200 continues to block 216, where the read of the molecule continues. At block 218, after the molecule has been read, it is determined (e.g., by the at least one processor 110) whether the expected "end" integrity marker was detected (where the expected "end" integrity marker may be the forward-oriented "end" integrity marker that indicates the end of a complete molecule, or, if the molecule was read backward, the reverse-oriented "begin" integrity marker). If so, then the read was successful, and the method 200 ends at block 220. At this point, the result of the readback can be provided to a calling system or requestor (e.g., a computer that initiated the retrieval of the data). If the expected "end" integrity marker was not detected, then the method 200 transitions to block 208, where the partial readback result is optionally placed into a temporary buffer (e.g., the buffer 115 shown in FIG. 1). As described above, after the block 208, the method 200 transitions to block 210, where it is determined whether more molecules are available, and, if so, a new molecule is selected at block 212, and, if not, the method 200 transitions to block 214 to either perform assembly (if warranted) or to abandon the readback of the molecule.

It is to be appreciated that integrity markers can also be inserted in other locations within the molecule. For example, assuming use of nucleic-acid molecules for storage, an integrity marker can be inserted after every N bases. This "intra-molecule" integrity marker can be distinct from the integrity markers used at the beginnings and ends of molecules so that a break that happens to occur at the beginning or end of an intra-molecule integrity marker is not mistaken as an integrity marker indicating the beginning or end of a complete molecule.

Figure 4:
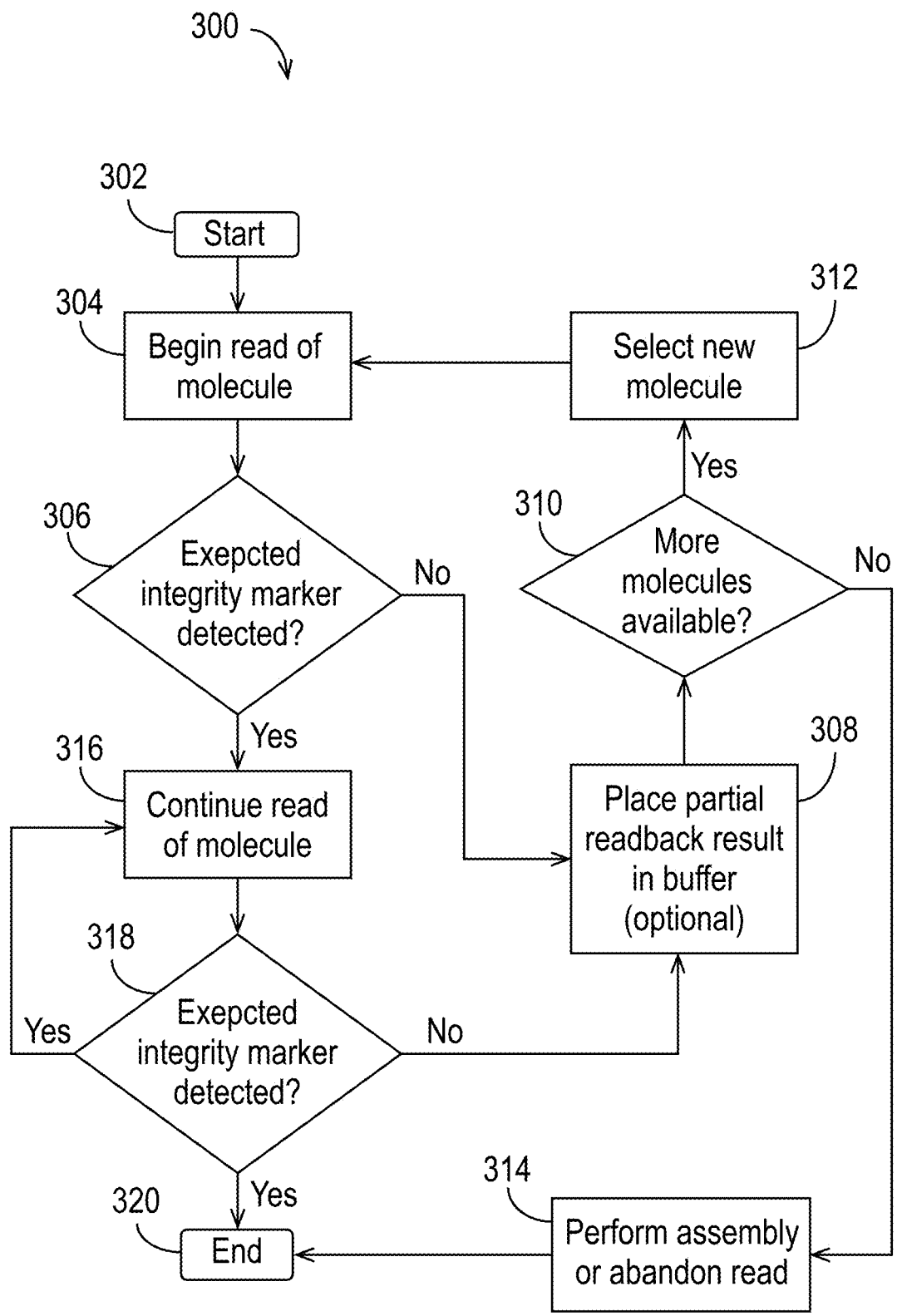
FIG. 4 is a flow diagram illustrating another example of a method performed by a molecular storage system in accordance with some embodiments.

FIG. 4 is a flow diagram illustrating an example of a method 300 performed by a molecular storage system (e.g., the molecular storage system 100) in accordance with some embodiments in which integrity markers are inserted periodically in molecules storing data. At block 302, the method 300 begins. At block 304, the reading of a molecule (e.g., the molecule 20 of FIG. 2) begins. At block 306, it is determined (e.g., by the at least one processor 110 of the molecular storage system 100) whether the expected integrity marker indicating the beginning (or end, indicated by the "end" integrity marker in reverse order) of a molecule is present. If not, at block 308, the in-progress read operation can be abandoned (e.g., by the at least one processor 110 instructing the read hardware 120 to stop the readback process). Optionally, the partial readback result may be placed into a buffer. Alternatively, as explained above, the partial readback result may be discarded. At block 310, if more molecules are available to read, the method 300 transitions to block 312, where another molecule is selected (e.g., if using read hardware 120 such as shown in FIG. 2, the voltage source 22 can be activated to draw another molecule 20 into the nanopore 15), and the method 300 returns to block 304. If, at 310, no more molecules are available, then the method 300 transitions to block 314, where an assembly procedure may be performed to attempt to recover the data (e.g., if the complexity/energy associated with doing so are warranted), or the read may be abandoned altogether.

If, at block 306, the expected integrity marker is detected (e.g., the at least one processor 110 finds either the "begin" integrity marker or a reverse-ordered "end" integrity marker), the method 300 continues to block 316, where the read of the molecule continues. At block 318, at a point during the readback (e.g., after a certain number of nucleotides), it is determined (e.g., by the at least one processor 110) whether an expected integrity marker was detected. If so, and the detected integrity marker does not indicate that the readback is complete (e.g., it is an intra-molecule integrity marker and not an "end" integrity marker or a reverse-oriented "begin" integrity marker), then the method 300 loops back to 316, and the readback continues. If the expected integrity marker was detected and indicated that the readback is complete, then the method 300 transitions to block 320, and the method 300 ends. At this point, the result of the readback can be provided to a calling system or requestor (e.g., a computer that initiated the retrieval of the data).

If, at block 318, the expected integrity marker (either an intra-sequence integrity marker or an "end" integrity marker (which, as explained above, could be a reverse-oriented "begin" integrity marker)) is not detected, then the method 300 moves to block 308, where, as explained above, the read of the molecule is abandoned, and the partial readback result is optionally placed into a temporary buffer (e.g., the buffer 115). Alternatively, the partial readback can be discarded. After the block 308, the method 300 transitions to block 310, where it is determined whether more molecules are available, and, if so, a new molecule is selected at block 312, and, if not, the method 300 transitions to block 314 to either perform assembly (if warranted) or to abandon the readback of the molecule.

It is to be understood that integrity markers can serve merely as markers that convey nothing other than a location (e.g., beginning, end, or intermediate position within a molecule), or they can also convey additional information, e.g., a tag for the data, a classification, file information, etc.

In the foregoing description and in the accompanying drawings, specific terminology has been set forth to provide a thorough understanding of the disclosed embodiments. In some instances, the terminology or drawings may imply specific details that are not required to practice the invention.

To avoid obscuring the present disclosure unnecessarily, well-known components are shown in block diagram form and/or are not discussed in detail or, in some cases, at all.

Unless otherwise specifically defined herein, all terms are to be given their broadest possible interpretation, including meanings implied from the specification and drawings and meanings understood by those skilled in the art and/or as defined in dictionaries, treatises, etc. As set forth explicitly herein, some terms may not comport with their ordinary or customary meanings.

As used in the specification and the appended claims, the singular forms "a," "an" and "the" do not exclude plural referents unless otherwise specified. The word "or" is to be interpreted as inclusive unless otherwise specified. Thus, the phrase "A or B" is to be interpreted as meaning all of the following: "both A and B," "A but not B," and "B but not A." Any use of "and/or" herein does not mean that the word "or" alone connotes exclusivity.

As used in the specification and the appended claims, phrases of the form "at least one of A, B, and C," "at least one of A, B, or C," "one or more of A, B, or C," and "one or more of A, B, and C" are interchangeable, and each encompasses all of the following meanings: "A only," "B only," "C only," "A and B but not C," "A and C but not B," "B and C but not A," and "all of A, B, and C."

To the extent that the terms "include(s)," "having," "has," "with," and variants thereof are used in the detailed description or the claims, such terms are intended to be inclusive in a manner similar to the term "comprising," i.e., meaning "including but not limited to."

The terms "exemplary" and "embodiment" are used to express examples, not preferences or requirements.

The term "coupled" is used herein to express a direct connection/attachment as well as a connection/attachment through one or more intervening elements or structures.

The terms "over," "under," "between," and "on" are used herein refer to a relative position of one feature with respect to other features. For example, one feature disposed "over" or "under" another feature may be directly in contact with the other feature or may have intervening material. Moreover, one feature disposed "between" two features may be directly in contact with the two features or may have one or more intervening features or materials. In contrast, a first feature "on" a second feature is in contact with that second feature.

The term "substantially" is used to describe a structure, configuration, dimension, etc. that is largely or nearly as stated, but, due to manufacturing tolerances and the like, may in practice result in a situation in which the structure, configuration, dimension, etc. is not always or necessarily precisely as stated. For example, describing two lengths as "substantially equal" means that the two lengths are the same for all practical purposes, but they may not (and need not) be precisely equal at sufficiently small scales (e.g., if the units of a measurement are meters, two features having lengths of 1.000 m and 1.001 m would have substantially equal lengths). As another example, a structure that is "substantially vertical" would be considered to be vertical for all practical purposes, even if it is not precisely at 90 degrees relative to horizontal.

The drawings are not necessarily to scale, and the dimensions, shapes, and sizes of the features may differ substantially from how they are depicted in the drawings.

Although specific embodiments have been disclosed, it will be evident that various modifications and changes may be made thereto without departing from the broader spirit and scope of the disclosure. For example, features or aspects of any of the embodiments may be applied, at least where practicable, in combination with any other of the embodiments or in place of counterpart features or aspects thereof. Accordingly, the specification and drawings are to be regarded in an illustrative rather than a restrictive sense.

The invention claimed is:

1. A molecular storage system, comprising:
   read hardware configured to read molecules storing data; and
   at least one processor coupled to the read hardware and configured to:
      determine whether a molecule currently being read by the read hardware includes an expected integrity marker; and
      in response to a determination that the molecule currently being read by the read hardware does not include the expected integrity marker, (a) identify the molecule currently being read by the read hardware as a fragment, and (b) instruct the read hardware to abandon reading the fragment.

2. The molecular storage system recited in claim 1, wherein the expected integrity marker indicates a beginning of the molecule currently being read by the read hardware or an end of the molecule currently being read by the read hardware.

3. The molecular storage system recited in claim 1, wherein the expected integrity marker comprises a unique sequence excluded by a coding scheme used to record data on molecules used in the molecular storage system.

4. The molecular storage system recited in claim 1, wherein the expected integrity marker comprises a sequence that does not naturally occur in molecules of a type used in the molecular storage system.

5. The molecular storage system recited in claim 1, wherein the expected integrity marker is an intra-molecule integrity marker.

6. The molecular storage system recited in claim 1, wherein the read hardware comprises:
   a nanopore;
   at least one electrode for sensing ionic current through the nanopore; and
   a voltage source coupled to the at least one electrode.

7. The molecular storage system recited in claim 1, further comprising at least one buffer coupled to the at least one processor, and wherein the at least one processor is further configured to:
   in response to the determination that the molecule currently being read by the read hardware does not include the expected integrity marker, store a partial readback result associated with the molecule currently being read by the read hardware in the at least one buffer.

8. The molecular storage system recited in claim 7, wherein the partial readback result is one of a plurality of partial readback results, and wherein the at least one processor is further configured to:
perform an assembly process using the plurality of partial readback results.

9. The molecular storage system recited in claim 8, wherein the at least one processor is further configured to:
before performing the assembly process, determine that no complete readback of another molecule storing identical data is available.

10. The molecular storage system recited in claim 7, wherein the expected integrity marker is a first integrity marker, and wherein the at least one processor is further configured to:
determine whether the molecule currently being read by the read hardware includes at least one additional integrity marker; and
in response to determining that the molecule currently being read by the read hardware includes both the first integrity marker and the at least one additional integrity marker, discard the partial readback result associated with the molecule currently being read by the read hardware.

11. The molecular storage system recited in claim 1, wherein the expected integrity marker is a first integrity marker, and wherein the at least one processor is further configured to:
determine whether the molecule currently being read by the read hardware includes at least one additional integrity marker; and
in response to determining that the molecule currently being read by the read hardware includes both the first integrity marker and the at least one additional integrity marker, provide a readback result to a calling system.

12. A method of reading molecules in a molecular storage system, the method comprising:
determining whether a molecule currently being read includes a first integrity marker indicating that a first end of the molecule currently being read is intact;
in response to determining that the molecule currently being read does not include the first integrity marker indicating that the first end of the molecule currently being read is intact, (a) identifying the molecule currently being read as a fragment, and (b) abandoning reading of the fragment;
in response to determining that the molecule currently being read includes the first integrity marker indicating that the first end of the molecule currently being read is intact, determining whether the molecule currently being read includes a second integrity marker indicating that a second end of the molecule currently being read is intact; and
in response to determining that the molecule currently being read includes the second integrity marker indicating that the second end of the molecule currently being read is intact, providing a read result to a requestor.

13. The method of claim 12, further comprising:
in response to determining that the molecule currently being read does not include the second integrity marker indicating that the second end of the molecule currently being read is intact, storing a partial readback result associated with the molecule currently being read.

14. The method of claim 13, wherein the partial readback result is one of a plurality of partial readback results, and wherein the method further comprises:
performing an assembly process using the plurality of partial readback results.

15. The method of claim 14, further comprising:
before performing the assembly process, determining that no complete readback of another molecule storing identical data is available.

16. The method of claim 12, wherein:
the first integrity marker is a forward-oriented integrity marker indicating a beginning of the molecule currently being read and the second integrity marker is a forward-oriented integrity marker indicating an end of the molecule currently being read, or
the first integrity marker is a reverse-oriented integrity marker indicating the end of the molecule currently being read and the second integrity marker is a reverse-oriented integrity marker indicating the beginning of the molecule currently being read.

17. The method of claim 12, wherein the first integrity marker and the second integrity marker are identical.

18. The method of claim 17, wherein the first integrity marker and the second integrity marker comprise a unique sequence excluded by a coding scheme used to record data on the molecules in the molecular storage system.

19. The method of claim 17, wherein the first integrity marker and the second integrity marker comprise a sequence that does not naturally occur in molecules of a type used in the molecular storage system.

20. The method of claim 12, wherein the first integrity marker and the second integrity marker are different.

21. The method of claim 12, further comprising:
determining whether the molecule currently being read includes an intra-molecule integrity marker; and
in response to determining that the molecule currently being read does not include the intra-molecule integrity marker, abandoning reading of the molecule currently being read.

* * * * *